(12) United States Patent
Ohyama et al.

(10) Patent No.: US 7,060,065 B2
(45) Date of Patent: Jun. 13, 2006

(54) RESECTSCOPE APPARATUS

(75) Inventors: Masahide Ohyama, Hino (JP); Kenji Harano, Hachioji (JP); Kazuya Hijii, Tama (JP)

(73) Assignee: Olympus Corporation, Tokyo (JP)

( * ) Notice: Subject to any disclaimer, the term of this patent is extended or adjusted under 35 U.S.C. 154(b) by 69 days.

(21) Appl. No.: 10/438,483

(22) Filed: May 15, 2003

(65) Prior Publication Data
US 2003/0233089 A1 Dec. 18, 2003

Related U.S. Application Data

(63) Continuation of application No. PCT/JP02/06038, filed on Jun. 18, 2002.

(51) Int. Cl.
*A61B 18/18* (2006.01)
(52) U.S. Cl. .......................................... 606/46; 606/41
(58) Field of Classification Search .................. 606/41, 606/45–48
See application file for complete search history.

(56) References Cited

U.S. PATENT DOCUMENTS

| | | | | |
|---|---|---|---|---|
| 5,810,764 A | * | 9/1998 | Eggers et al. .................. | 604/23 |
| 5,919,191 A | * | 7/1999 | Lennox et al. ................. | 606/48 |
| 5,944,715 A | * | 8/1999 | Goble et al. ................... | 606/41 |
| 5,976,129 A | * | 11/1999 | Desai ........................... | 606/40 |
| 6,004,319 A | * | 12/1999 | Goble et al. ................... | 606/48 |
| 6,113,597 A | | 9/2000 | Eggers et al. | |
| 6,261,286 B1 | * | 7/2001 | Goble et al. ................... | 606/34 |
| 6,471,701 B1 | * | 10/2002 | Brommersma et al. ....... | 606/46 |
| 6,491,690 B1 | * | 12/2002 | Goble et al. ................... | 606/41 |
| 6,736,810 B1 | * | 5/2004 | Hoey et al. .................... | 606/34 |

FOREIGN PATENT DOCUMENTS

| | | |
|---|---|---|
| JP | 4-45694 | 10/1992 |
| JP | 2000-201946 | 7/2000 |
| JP | 2002-177297 | 6/2002 |
| WO | WO 97/00646 | 1/1997 |
| WO | WO 99/16371 | 4/1999 |

* cited by examiner

*Primary Examiner*—Michael Peffley
(74) *Attorney, Agent, or Firm*—Scully, Scott, Murphy & Presser, P.C.

(57) ABSTRACT

In a resectscope apparatus of the present invention, by using an output from a second output transformer, high frequency current passes through a treating electrode when the treating electrode is in contact with a living tissue in a conductive liquid. Then, the high frequency current flows between the treating electrode and a return electrode. Thus, the treating electrode generates heat. Bubbles are formed from the conductive liquid on the peripheral surface of the treating electrode and cover the treating electrode. Interlelectrode resistance increases from a resistance and becomes higher resistance to a substantially insulating state. Then, the voltage increases, and discharging occurs between the treating electrode and the living tissue. By using the high frequency current from the discharging, the living tissue is treated.

10 Claims, 7 Drawing Sheets

RESECTSCOPE APPARATUS

CROSS REFEERENCE TO RELATED APPLICATION

This application is a continuation of PCT application no. PCT/JP02/06038 filed on Jun. 18, 2002, the entire contents of which is incorporated herein by its reference.

TECHNICAL FIELD

The present invention relates to a resectscope apparatus for incising, resecting, and transpiring body tissue by using an endoscope.

BACKGROUND ART

In general, a resectscope is used for transurethral resection (TUR) and transcervical resection (TCR). The resectscope mainly includes an optical scope (sometimes simply called scope), which is an endoscope for observation, and an electrode unit for resecting living body tissue.

As the resectscope, for example, Japanese Examined Utility Model Registration Application Publication No.4-45694 discloses an electrode for rigid scope surgical instrument having a rigid heat-resistance member between a distal end portion of an electric insulative member and an elemental wire. The rigid heat-resistance member is in contact with the periphery of the elemental wire. Thus, burns of the electric insulating member can be prevented.

When the resectscope is used for resecting the prostate, for example, D-sorbitol which is insulating transparent liquid as a perfusion fluid may be supplied for expanding the inside of a narrow cavity. Thus, the cavity is expanded, and a sheath of the resectscope can be inserted into the cavity.

Then, the surface of a lesion is observed by using a scope located within the sheath. At the same time, high frequency current passes through a treating electrode of an electrode unit located at a distal end portion opening of the sheath. By discharging, current flows from the treating electrode to an external electrode located outside of a body through the liquid filled within the cavity. Then, the operating portion is manipulated to move the treating electrode back and forth for treating the lesion.

Here, because the perfusion fluid filled within a cavity is an insulative liquid, the distribution of current traveling from the treating electrode to the external electrode can be prevented. Thus, more efficient treatment can be performed.

However, when a treatment is performed by filling an insulative liquid within a cavity, and when the treating time is longer, the liquid is absorbed into a blood vessel, which may have bad influences on a human body. Therefore, the operation time is limited.

In order to overcome the problem, a physiological saline, which is a conductive liquid, may be filled within a cavity as a perfusion fluid. However, when the conductive liquid is filled within a cavity, current to flow from the treating electrode to the external electrode disperses through the liquid. Therefore, discharging does not occur on a lesion, thus disadvantageously cannot achieve effective treatment.

Thus, Japanese Unexamined Patent Application Publication No. 2000-201946 discloses a resectscope apparatus including a treating electrode and a return electrode. The treating electrode is located in the vicinity of a long, narrow and hollow sheath distal end portion to be inserted into a body cavity filled with a conductive liquid. The treating electrode treats a body tissue by using high frequency cauterization current. The return electrode is provided within the conductive liquid and receives current from the treating electrode. An insulating portion is provided on at least a non-contact surface of the body tissue of the treating electrode. Thus, high frequency current supplied to the treating electrode within the cavity filled with the conductive liquid does not leak from the insulating portion on the non-contact surface of the body tissue to the liquid. The high frequency current is efficiently discharged from the body tissue contact surface of the treating electrode which is in contact with a body tissue. The high frequency current flows to the return electrode.

Figure 12:
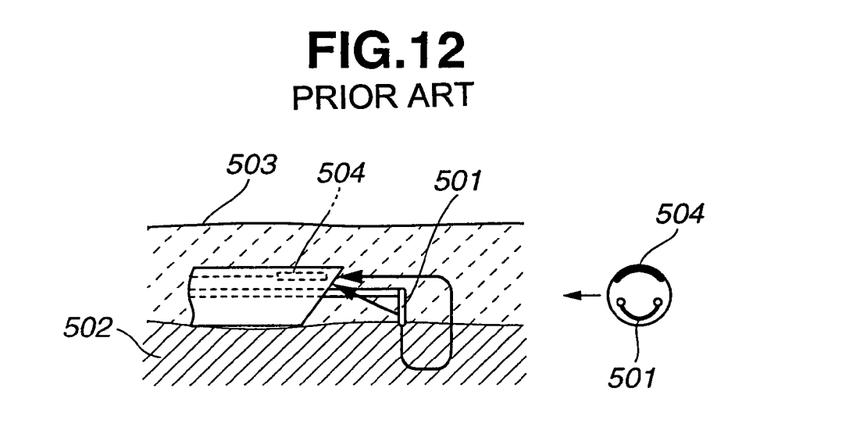
FIG. 12 is a diagram for describing an operation of a treating electrode by conventional power supply.

However, as shown in FIG. 12, in order to prevent high frequency current supplied to a treating electrode 501 from returning to a return electrode 504 not through a body tissue 502 but directly through a conductive liquid 503, the resectscope apparatus according to Japanese Unexamined Patent Application Publication No. 2000-201946 includes an insulating portion at least on a body tissue non-contact surface of the treating electrode. However, the insulating portion on the non-contact surface of the body tissue is complicated in structure. Therefore, the manufacturing is disadvantageously difficult in effect.

The present invention is made in view of the above-described problems. It is an object of the present invention to provide a resectscope apparatus, which has a simple structure and is inexpensive, for treating a lesion effectively without adverse effects of an insulative liquid on a human body and without limitation on an operation time.

DISCLOSURE OF INVENTION

In a resectscope apparatus of the present invention, by using an output from a second output transformer, high frequency current passes through a treating electrode when the treating electrode is in contact with a living tissue in a conductive liquid. Then, the high frequency current flows between the treating electrode and a return electrode. Thus, the treating electrode generates heat. Bubbles are formed from the conductive liquid on the peripheral surface of the treating electrode and cover the treating electrode. Interelectrode resistance increases from a predetermined resistance value R1 and becomes higher resistance to a substantially insulating state. Then, the voltage increases, and discharging occurs between the treating electrode and the living tissue. By using the high frequency current caused by the discharging, the living tissue is treated.

BRIEF DESCRIPTION OF THE DRAWINGS

FIGS. 8(*a*) and 8(*b*) are diagrams showing waveforms of signals output from a waveform circuit to a high frequency generating circuit in FIG. 3;

FIGS. 10(*a*) and 10(*b*) are diagrams for describing an operation of a treating electrode by using power supplied from a second output transformer in FIG. 5;

BEST MODE FOR CARRYING OUT THE INVENTION

An embodiment of the invention will be described below with reference to drawings.

Figure 1:
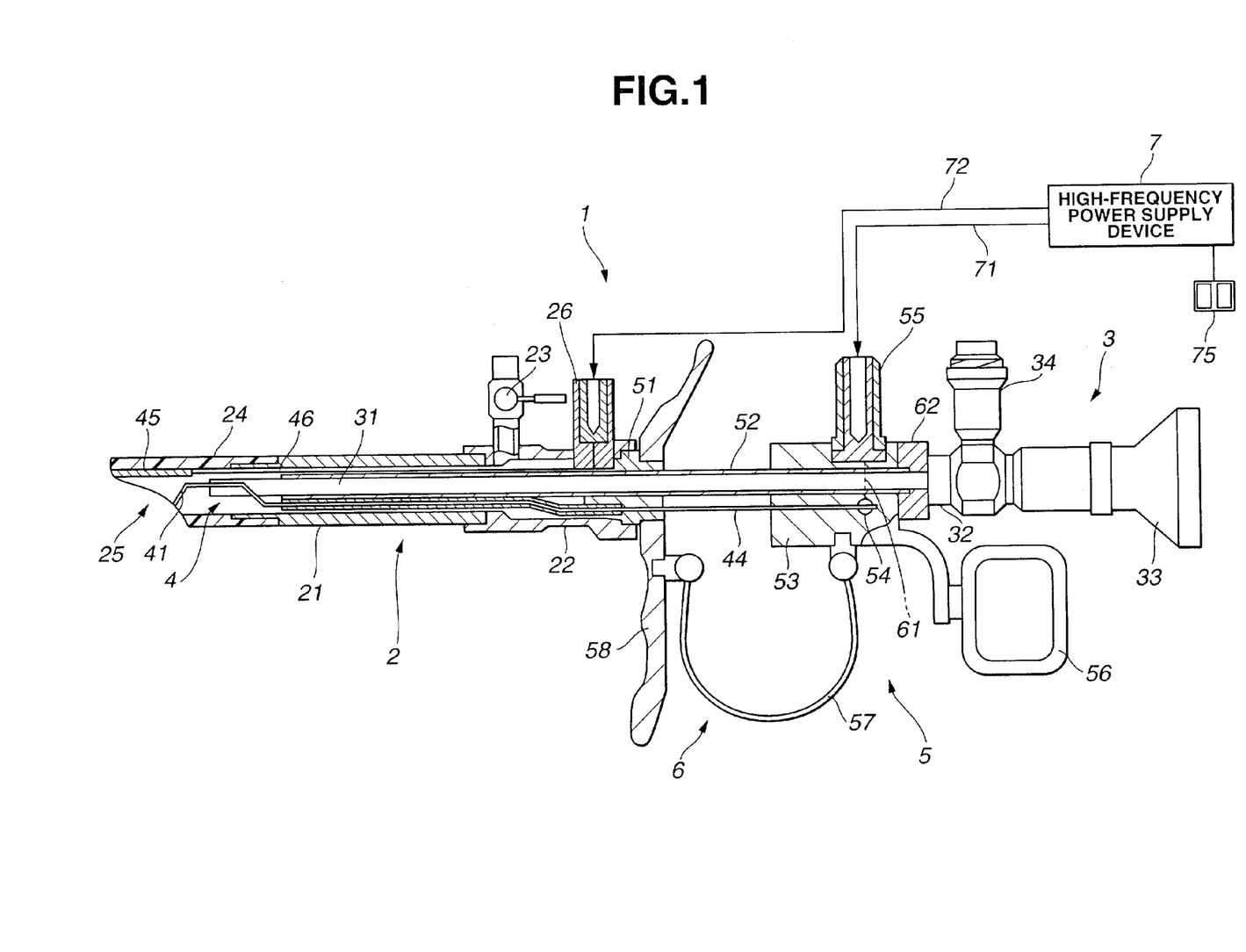
FIG. 1 is a configuration diagram showing a configuration of a resectscope apparatus according to an embodiment of the present invention.
Figure 2:
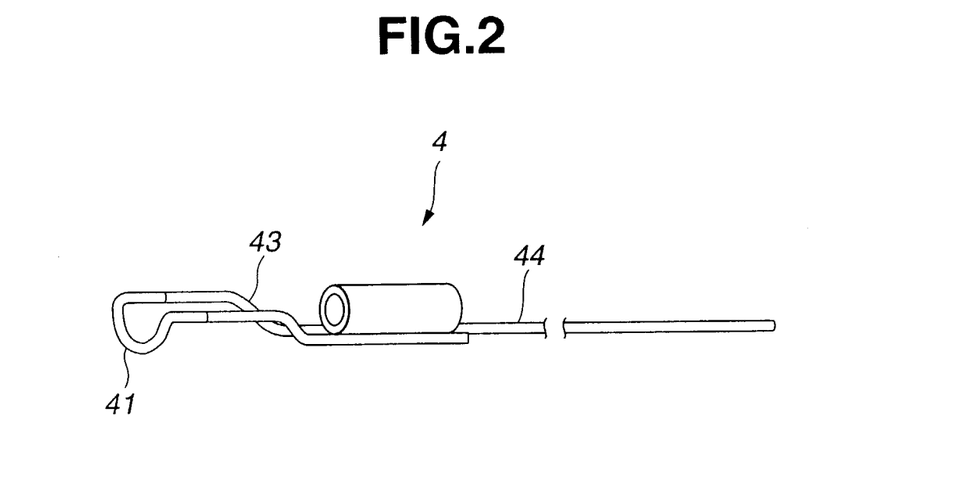
FIG. 2 is a configuration diagram showing a configuration of a treating electrode in FIG. 1.
Figure 3:
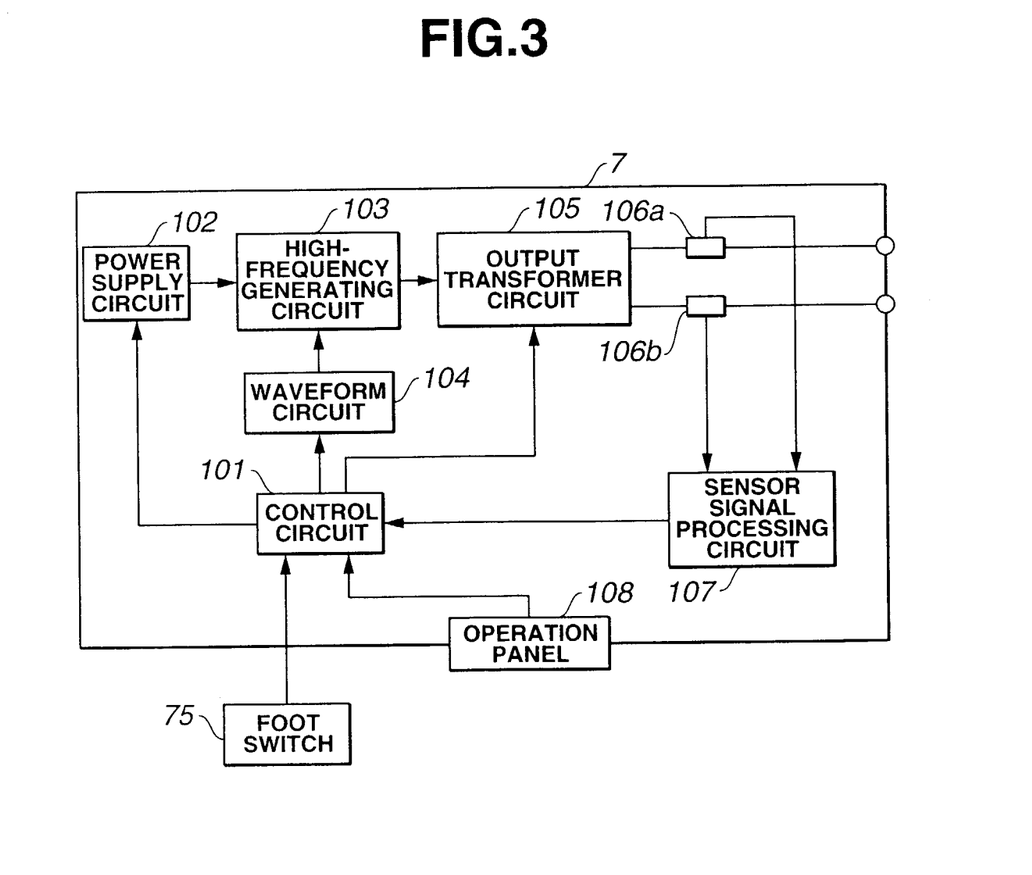
FIG. 3 is a configuration diagram showing a configuration of a high frequency power supply device in FIG. 1.
Figure 4:
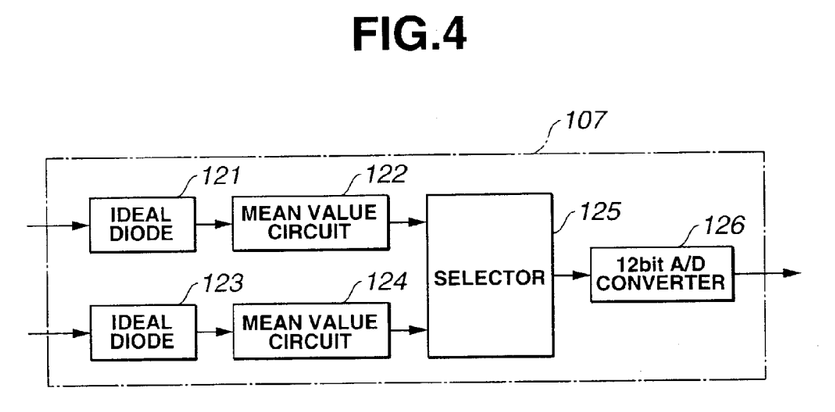
FIG. 4 is a configuration diagram showing a configuration of a sensor signal processing circuit in FIG. 3.
Figure 5:
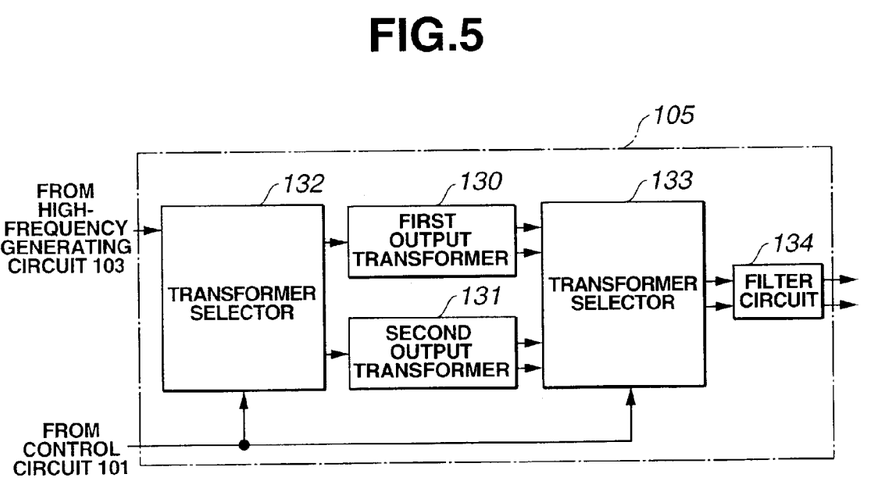
FIG. 5 is a configuration diagram showing a configuration of an output transformer circuit in FIG. 3.
Figure 6:
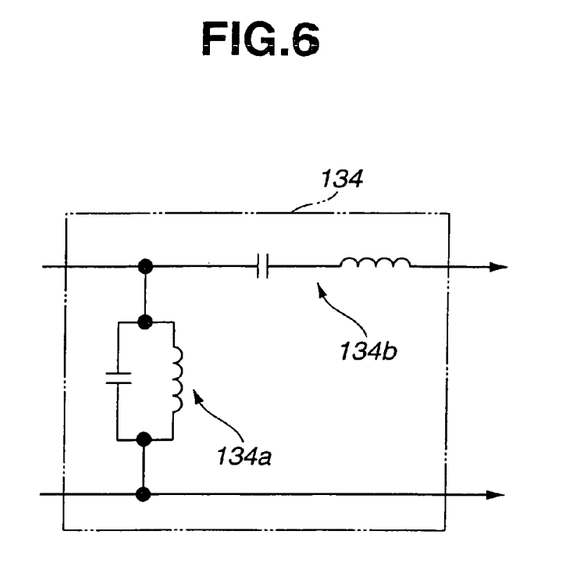
FIG. 6 is a configuration diagram showing a configuration of a filter circuit in FIG. 5.
Figure 7:
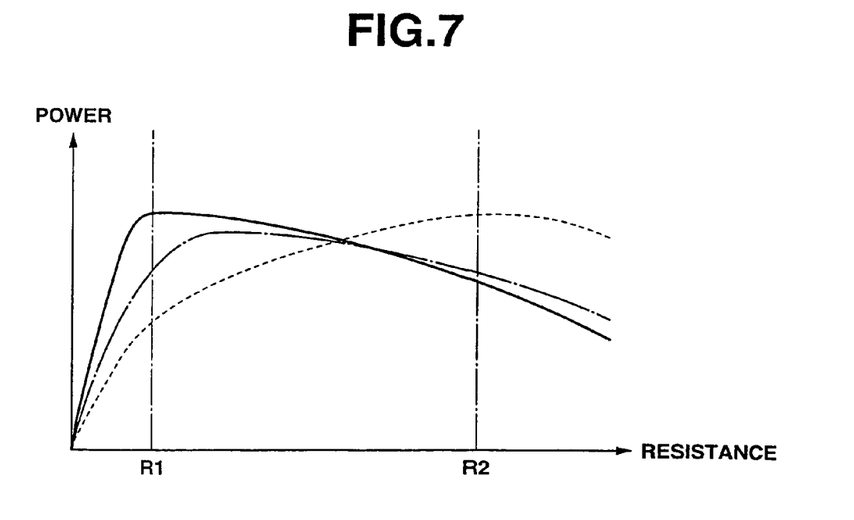
FIG. 7 is a diagram showing load characteristics of power supply in the output transformer circuit in FIG. 3.
Figure 8A:
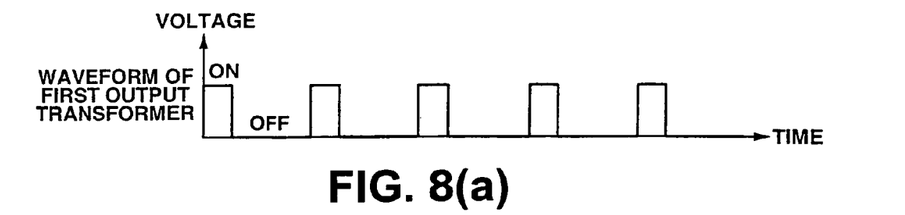
Figure 8B:
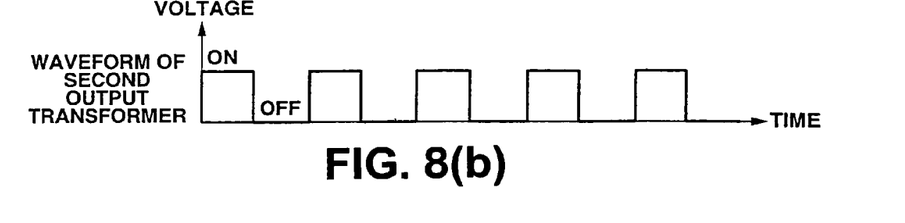
Figure 9:
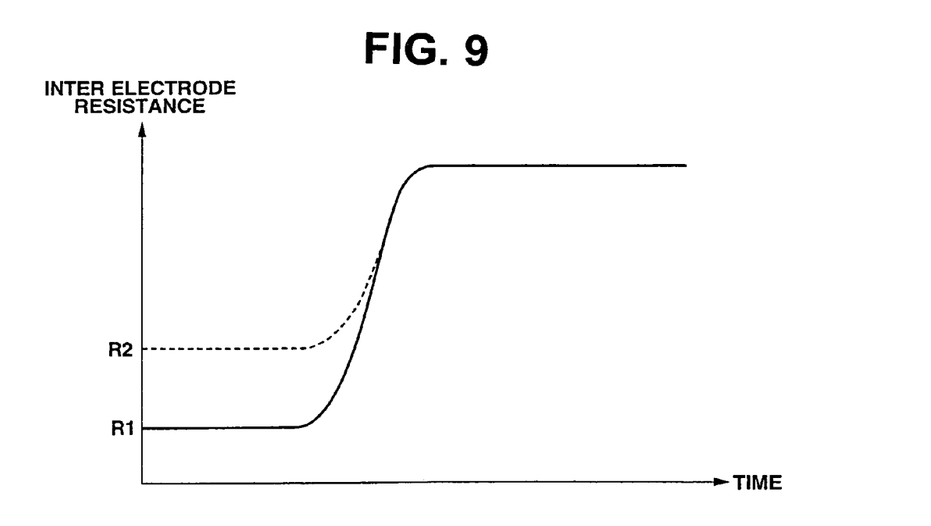
FIG. 9 is a diagram showing time changes of interelectrode resistance by power supply having load characteristics in FIG. 7.
Figure 10A:
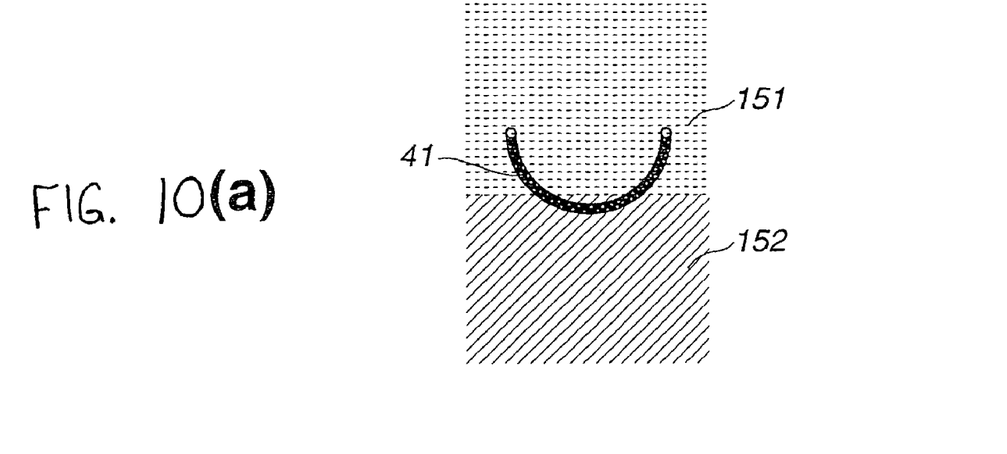
Figure 10B:
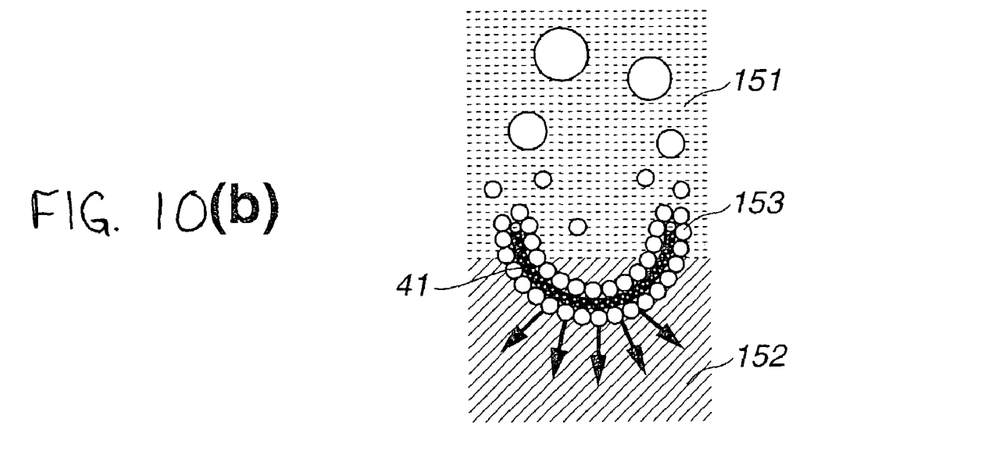
Figure 11:
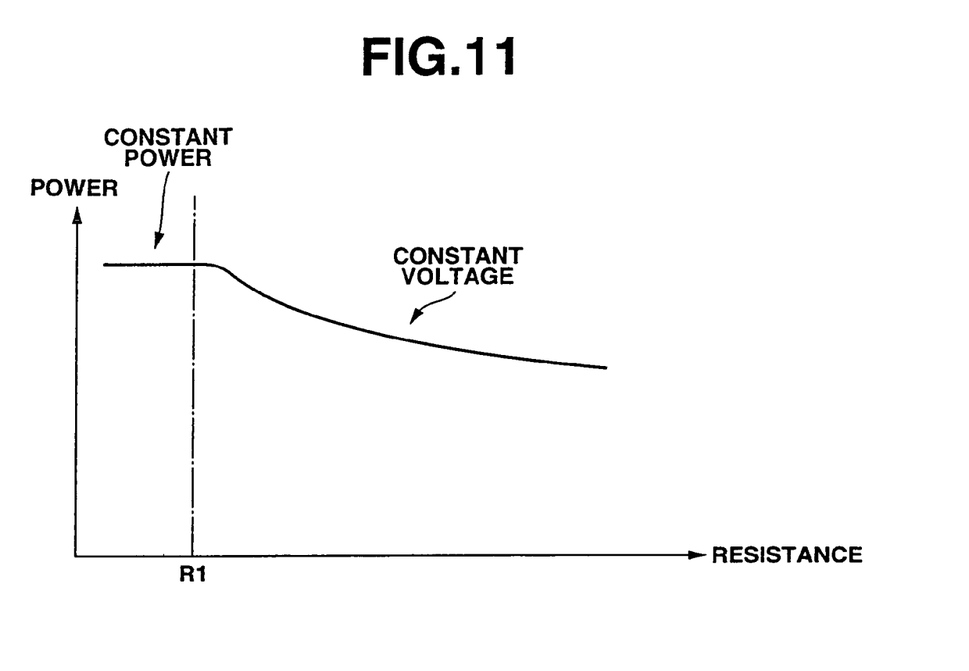
FIG. 11 is a diagram showing a variation of the load characteristic of supply power in the output transformer circuit in FIG. 3.

First of all, FIGS. 1 to 11 relate to an embodiment of the invention. FIG. 1 is a configuration diagram showing a configuration of a resectscope apparatus. FIG. 2 is a configuration diagram showing a configuration of a treating electrode in FIG. 1. FIG. 3 is a configuration diagram showing a configuration of a high frequency power supply device in FIG. 1. FIG. 4 is a configuration diagram showing a configuration of a sensor signal processing circuit in FIG. 3. FIG. 5 is a configuration diagram showing a configuration of an output transformer circuit in FIG. 3. FIG. 6 is a configuration diagram showing a configuration of a filter circuit in FIG. 5. FIG. 7 is a diagram showing load characteristics of power supply in the output transformer circuit in FIG. 3. FIGS. 8(*a*) and 8(*b*) are diagrams showing waveforms of signals output from a waveform circuit to a high frequency generating circuit in FIG. 3. FIG. 9 is a diagram showing time changes of interelectrode resistance by power supply having load characteristics in FIG. 7. FIGS. 10(*a*) and 10(*b*) are diagrams for describing an operation of a treating electrode by using power supplied from a second output transformed in FIG. 5. FIG. 11 is a diagram showing a variation of the load characteristic of supply power in the output transformer circuit in FIG. 3.

As shown in FIG. 1, a resectscope apparatus 1 mainly includes a resectscope 6 and a high frequency power supply device 7. The resectscope 6 includes a hollow sheath 2, a scope 3, an electrode unit 4, a return electrode 45, and a handle portion 5. The hollow sheath 2 has a through-hole. The scope 3 is provided within the hole and is used for observing a lesion or the like. The electrode unit 4 includes a treating electrode 41 on the distal end side. The treating electrode 41 is a long and narrow wire-shaped electrode for treating a lesion. The return electrode 45 is provided within the hole at the distal end of the sheath 2. Current output from the treating electrode 41 returns to the return electrode 45. The handle portion 5 is included in an operating portion. The high frequency power supply device 7 is an energizing unit for the treating electrode 41 of the electrode unit 4. Feedback current from the return electrode 45 returns to the high frequency power supply device 7. ON and OFF of power supply from the high frequency power supply device 7 to the treating electrode 42 of the electrode unit 4 is controlled by a foot switch 75 connected to the high frequency power supply device 7.

The sheath 2 includes an inserting portion 21 and a hand-side body portion 22. The inserting portion 21 is inserted into a body cavity through, for example, the urethra. The hand-side body portion 22 is provided at the back end of the inserting portion 21. A water-supply end fitting 23 having a cock is provided on the periphery of the hand-side body portion 22. The water-supply end fitting 23 supplies, for example, conductive physiological saline as a perfusion fluid to the treating portion.

The scope 3 and the electrode unit 4 lies through the inserting portion 21. A distal end member 24 is provided at the distal end of the inserting portion 21. The distal end member 24 includes an insulating member such as a rigid resin member.

The scope 3 includes a rigid inserting tube 31 and a hand-side portion 32. The inserting tube 31 is long and narrow and has an observation optical system built in. The inserting tube 31 lies through the inserting portion 21 and the distal end member 24. The hand-side portion 32 is provided at the proximal end of the inserting tube 31. An eyepiece portion 33 is provided at the proximal end of the hand-side portion 32. An operator uses the eyepiece portion 33 to make visual observations. A light guide connecting portion 34 is provided on the side portion of the hand-side portion 32. A light guide, not shown, is connected to the light guide connecting portion 34 freely removably for supplying illumination light for observation.

The electrode unit 4 lies through the inserting portion 21. As shown in FIGS. 1 and 2, the electrode unit 4 mainly includes the treating electrode 41, a bifurcate arm member 43, and a long and narrow metal pipe 44. The treating electrode 41 is placed on the distal end side and is a rigid metal member in a loop shape. The bifurcate arm member 43 fixes the treating electrode 41 and holds a positional relationship of the treating electrode 41 with respect to an inserting axis of the scope 3. One end of the bifurcate arm member 43 on the distal end side has a rigid and transparent hole and bifurcates. The proximal end of the bifurcate arm member 43 is provided at the distal end of the metal pipe 44. An insulating tube, not shown, covers the periphery of the metal pipe 44. The proximal end of the metal pipe 44 is exposed at the back end of the insulating tube as an electrode connecting portion.

The electrode unit 4 is provided within the inserting portion 21 such that the electrode unit 4 can move back and forth. The treating electrode 41 is provided freely retractably at a distal end portion opening 25 of the sheath 2.

The treating electrode 41 and the bifurcate arm member 43 are provided at the distal end of the metal pipe 44. A slider 53 is provided at the proximal end of the metal pipe 44. The slider lies through the inserting portion 21 and the hand-side body portion 22 and extends from the proximal end surface of the hand-side body portion 22. The slider 53 will be described later.

The handle portion 5 mainly includes a sheath connecting portion 51, a guide tube 52 and the slider 53. The sheath connecting portion 51 is freely removably connected to the hand-side body portion 22 of the sheath 2. The guide tube 52 projects from the back end surface of the sheath connecting portion 51. The inserting tube 31 lies through the guide tube 52. The slider 53 has substantially a pipe form and is held freely slidably by the guide tube 52.

The slider 53 includes an electrode fixing portion 54, a connector 55 for high frequency power supply and a thumb-hook ring 56. The electrode fixing portion 54 electrically connects to the electrode connecting portion at the back end of the electrode unit 4. A power supply cord 71 extending from the high frequency power supply device 7 is freely removably connected to the connector 55. An operator puts his/her thumb through the ring-shaped thumb-hook ring 56.

The slider 53 and the sheath connecting portion 51 are connected through a flat spring 57. In other words, one end of the flat spring 57 is fixed to a finger hook 58 which has a lever shape and which is fixed at the sheath connecting portion 51 integrally. The other end is fixed to the slider 53. Thus, the flat spring 57 always applies a force to the slider 53 toward the eyepiece portion 33 side.

Therefore, by appropreately operating the thumb-hook ring 56 in the slider 53, the slider 53 is manipulated to move back and forth. Then, the treating electrode 41 of the electrode unit 4 moves back and forth to project and retract from the distal end portion opening 25 of the sheath 2.

A feedback current connector 26 is provided on the periphery of the hand-side body portion 22. A feedback current cord 72 extends from the high frequency power supply device 7 and is freely removably connected to the feedback current connector 26. The feedback current connector 26 and the return electrode 45 are electrically connected through a lead line 46 indicated by a solid line, for example.

On the other hand, the high frequency power supply connector 55 and the electrode fixing portion 54 are electrically connected through a lead line 61 indicated by a broken line, for example. Thus, when the power supply cord 71 of the high frequency power supply device 7 is connected to the connector 55 for high frequency power supply, the power supply cord 71 and the treating electrode 41 of the electrode unit 4 are electrically conducted. Then, a lesion can be treated. In this case, leak current can be measured by calculating a difference between values of current supplied to the treating electrode 41 and feedback current.

Furthermore, a slider positioning fixing member 62 is provided at the proximal end of the guide tube 52. The slider positioning fixing member 62 can prevent the slider 53 from falling out from the guide tube 52. Additionally, the hand-side portion 32 of the inserting tube 31 within the guide tube 52 is fixed integrally to the slider positioning fixing member 62.

As shown in FIG. 3, the high frequency power supply device 7 includes a control circuit 101, a power supply circuit 102, a high frequency generating circuit 103, a waveform circuit 104, an output transformer circuit 105, current sensors 106a and 106b and a sensor signal processing circuit 107. The control circuit 101 controls power supply in response to signals from the foot switch 75. The power supply circuit 102 is controlled by the control circuit 101 and generates direct current power. The high frequency generating circuit 103 switches direct current power from the power supply circuit 102 and generates high frequency power. The waveform circuit 104 is controlled by the control circuit 101 and supplies to the high frequency generating circuit 103 waveform signals of high frequency power generated by the high frequency generating circuit 103. The output transformer circuit 105 amplifies high frequency voltage of the high frequency power generated by the high frequency generating circuit 103 and applies the voltage between the treating electrode 41 and the return electrode 45. Then, the output transformer circuit 105 supplies high frequency current to the treating electrode 41. Each of the current sensors 106a and 106b detects high frequency current output from the output transformer circuit 105. The sensor signal processing circuit 107 A/D converts current values detected by the current sensors 106a and 106b. Based on digitized current data from the sensor signal processing circuit 107, the control circuit 101 controls the power supply circuit 102 and the waveform circuit 104.

As shown in FIG. 4, the sensor signal processing circuit 107 includes an ideal diode 121, a mean value circuit 122, an ideal diode 123, a mean value circuit 124, a selector 125, and a 12-bit A/D converter 126. The ideal diode 121 smoothes current, which flows, for example, from the treating electrode 41 to a living body tissue and which is detected by the current sensor 106a. The mean value circuit 122 integrates and averages outputs of the ideal diode 121. The ideal diode 123 smoothes current, which is detected by the current sensor 106b and which is collected, for example, by the output transformer circuit 105 side. The mean value circuit 124 integrates and averages outputs of the ideal diode 123. The selector 125 selectively outputs signals from the mean value circuit 122 and the mean value circuit 124. The 12 bit A/D converter 126 converts signals output from the selector 125 to 12-bit digital data and outputs to the control circuit 101.

As shown in FIG. 5, the output transformer circuit 105 has two output transformers including a first output transformer 130 and a second output transformer 131. When a select switch, not shown, on an operation panel 108 (see FIG. 3) is pressed, a select signal is input to the control circuit 101. Under the control of the control circuit 101, the transformer selectors 132 and 133 of the output transformer circuit 105 are switched. Either one of the output transformers is selected. High frequency current is output through a filter circuit 134. As shown in FIG. 6, the filter circuit 134 includes a parallel resonating circuit 134a and a serial resonating circuit 134b.

In addition to the resectscope 6, a conventional resect scope may be connected to the high frequency power supply apparatus 7 of the resectscope apparatus 1 according to this embodiment. In this case, the conventional resectscope has an external electrode outside of a body and a treating electrode within an insulative liquid such as D-sorbitol filled within a cavity. The first output transformer 130 is selected when the conventional resectscope is used by using an insulative liquid. As shown by a load characteristic indicated by a broken line in FIG. 7, the control circuit 101 controls the power supply circuit 102 and the waveform circuit 104 such that power supply can be maximum at a resistance R2 of the insulative liquid. A waveform output from the waveform circuit 104 to the high frequency generating circuit 103 here is shown in FIG. 8(a).

By using the power having the load characteristic, high frequency current passes through the treating electrode of the conventional resectscope in contact with a living tissue by using the insulative liquid. Then, the high frequency current flows between the treating electrode and the external electrode. The treating electrode generates heat, and the living tissue is burned. As indicated by a broken line in FIG. 9, the interelectrode resistance between the treating electrode and the external electrode increases from the resistance R2 and becomes high resistance. Then, the voltage increases, and discharging occurs between the treating electrode and the living tissue. By using the high frequency current from the discharging, the living tissue is resected and coagulated for treatment.

The second output transformer 131 is selected when the resectscope 6 according to this embodiment is used by using a conductive liquid such as physiological saline. The control circuit 101 controls the power supply circuit 102 and the waveform circuit 104 such that the power supply can be maximum at the resistance R1 of the conductive liquid as shown by the load characteristic indicated by the solid line in FIG. 7. A waveform output from the waveform circuit 104 to the high frequency generating circuit 103 here is shown in FIG. 8(b).

When switching is performed in the high frequency generating circuit 103 by using the waveform shown in FIG. 8(a), the load characteristic of the power supply from the second output transformer 131 changes as indicated by a one-dotted chain line in FIG. 7. Thus, switching is performed in the high frequency generating circuit 103 by using the waveform shown in FIG. 8(b).

By using the power having the load characteristic of the second output transformer 131, high frequency current passes through the treating electrode 41 when the treating electrode 41 of the resectscope 6 according to this embodiment is in contact with a living tissue 152 as shown in FIG. 10(a). Then, the high frequency current flows between the treating electrode 41 and the return electrode 45, and the treating electrode 41 generates heat. As shown in FIG. 10(b), bubbles 153 are formed from a conductive liquid 151 on the peripheral surface of the treating electrode 41 and cover the treating electrode 41. As indicated by a solid line in FIG. 9, interelectrode resistance between the treating electrode 41 and the return electrode 45 increases from a resistance R1 and becomes high resistance to a substantially insulating state. Then, the voltage increases, and discharging occurs between the treating electrode 41 and the living tissue 152. By using the high frequency current from the discharging, the living tissue is resected and is coagulated for treatment.

Here, for example, the treating electrode 41 has a semicircular form of about 6 mm in diameter including a cotton material of φ 0.25 mm in thickness. When the conductive liquid 151 has a load resistance not more than (R1=)100 Ω, a maximum power supply (at R1) from the second output transformer 131 is arranged to be larger than 200 W.

In this way, according to this embodiment, the bubbles 153 are formed from the conductive liquid 151 on the peripheral surface of the treating electrode 41 in contact with the living tissue 152 in the conductive liquid 151 in order to obtain the substantially insulated state. Then, the living tissue is treated by using the high frequency current from discharging. Therefore, the structure of the treating electrode 41 is simple and inexpensive. Additionally, a lesion can be treated effectively without adverse influences of the insulative liquid on a human body and without limitation on an operation time.

The load characteristic of power supply of the second output transformer 131 is not limited to the load characteristic indicated by the solid line in FIG. 7. As shown in FIG. 11, the load characteristic may have constant power until about the resistance R1. Then, power may be supplied at a constant voltage. By using the load characteristic, a conductive liquid can be vaporized by an easy operation in a stable manner.

The embodiment of the invention has been described above. However, the invention is not limited to the above-described embodiment. Various changes may be apparently made without departing from the spirit of the invention.

INDUSTRIAL APPLICABILITY

According to the present invention as described above, the resectscope apparatus can be provided, which has a simple structure and is inexpensive, for treating a lesion effectively without adverse effects of an insulative liquid on a human body and without limitation on an operation time.

The invention claimed is:

1. A resectscope apparatus, comprising:
    two electrodes adapted to be provided in a conductive or insulating solution within a body cavity; and
    a high frequency power supply device having a load characteristic, including:
        a power supply for supplying high frequency current to a living tissue to resect and coagulate the living tissue; and
        a control unit for controlling the load characteristic to discharge the high frequency current to the living tissue from at least one of the two electrodes, the control unit having a first control circuit which, in the case where the solution is conducive, performs controlling of the load characteristic in correspondence with a resistance value of the conductive solution so as to vaporize the conductive solution in the vicinity of a peripheral surface of at least one of the two electrodes in order to change the resistance value between the two electrodes, a second control circuit which, in the case where the solution is insulating, performs controlling of the load characteristic in correspondence with a resistance value of the insulating solution in order to change the resistance value between the two electrodes, and a switching control portion for selectively switching activations of the first and second control circuits depending upon whether the solution is conductive or insulating.

2. A resectscope apparatus according to claim 1, wherein the control unit controls the load characteristic such that the electric power of the high frequency current is maximum when the resistance value between the two electrodes is at an initial value and becomes smaller as the resistance value increases from the initial value to a final value.

3. A resectscope apparatus according to claim 1, wherein the control unit controls the load characteristic such that the electric power of the high frequency current is maximum when the resistance value between the two electrodes is at an initial value and is maintained at a constant value as the resistance value increases from the initial value to a final value.

4. A resectscope apparatus according to claim 1, further comprising a sensor for detecting the high frequency current, wherein the control unit controls the load characteristic based on information obtained by the sensor.

5. A resectscope apparatus, comprising:
    two electrodes adapted to be provided in a conductive or insulating solution within a body cavity; and
    a high frequency power supply device having a load characteristic, including:
        a power supply for supplying high frequency current to a living tissue to resect and coagulate the living tissue; and
        a control unit for controlling the load characteristic to discharge the high frequency current to the living tissue from at least one of the two electrodes, wherein the control unit can switch between a first control mode and a second control mode, the first control mode being the one, in the case where the solution is conductive, for performing controlling of the load characteristic in correspondence with the characteristic of the conductive solution, the second control mode being the one, in the case where the solution is insulating, for performing controlling of the load characteristic in correspondence with the characteristic of the insulating solution.

6. A resectscope apparatus according to claim 5, wherein the control unit further comprising:
- a first control circuit for controlling the load characteristic in correspondence with the first control mode;
- a second control circuit for controlling the load characteristic in correspondence with the second control mode; and
- a switching control portion for selectively switching electrical connections to the first and second control circuits depending upon whether the solution is conductive or insulating, thereby to activate either one of the first and second control circuits.

7. A resectscope apparatus according to claim 5, wherein the control unit controls the load characteristic such that the electric power of the high frequency current is maximum when the resistance value between the two electrodes is at an initial value and becomes smaller as the resistance value increases from the initial value to a final value.

8. A resectscope apparatus according to claim 5, wherein the control unit controls the load characteristic such that the electric power of the high frequency current is maximum when the resistance value between the two electrodes is at an initial value and is maintained at a constant value as the resistance value increases from the initial value to a final value.

9. A resectscope apparatus according to claim 6, wherein the control unit controls the load characteristic such that the electric power of the high frequency current is maximum when the resistance value between the two electrodes is at an initial value and becomes smaller as the resistance value increases from the initial value to a final value.

10. A resectscope apparatus according to claim 6, wherein the control unit controls the load characteristic such that the electric power of the high frequency current is maximum when the resistance value between the two electrodes is at an initial value and is maintained at a constant value as the resistance value increases from the initial value to a final value.

* * * * *